(12) United States Patent
Costantini

(10) Patent No.: US 11,324,492 B2
(45) Date of Patent: May 10, 2022

(54) MULTIFUNCTIONAL SURGICAL INSTRUMENT

(71) Applicant: Raffaele Costantini, Chieti (IT)

(72) Inventor: Raffaele Costantini, Chieti (IT)

( * ) Notice: Subject to any disclaimer, the term of this patent is extended or adjusted under 35 U.S.C. 154(b) by 402 days.

(21) Appl. No.: 16/612,787

(22) PCT Filed: May 9, 2018

(86) PCT No.: PCT/IT2018/000068
§ 371 (c)(1),
(2) Date: Nov. 12, 2019

(87) PCT Pub. No.: WO2018/216039
PCT Pub. Date: Nov. 29, 2018

(65) Prior Publication Data
US 2020/0146665 A1 May 14, 2020

(30) Foreign Application Priority Data

May 26, 2017 (IT) ........................ 102017000057439

(51) Int. Cl.
| | |
|---|---|
| *A61B 17/02* | (2006.01) |
| *A61B 17/28* | (2006.01) |
| *A61B 17/00* | (2006.01) |
| *A61B 17/29* | (2006.01) |
| *A61B 18/00* | (2006.01) |
| *A61B 18/14* | (2006.01) |
| *A61B 17/32* | (2006.01) |

(52) U.S. Cl.
CPC ...... *A61B 17/0218* (2013.01); *A61B 17/0281* (2013.01); *A61B 17/282* (2013.01); *A61B 18/1482* (2013.01); *A61B 2017/00929* (2013.01); *A61B 2017/2911* (2013.01); *A61B 2017/320052* (2013.01); *A61B 2018/00541* (2013.01); *A61B 2018/00601* (2013.01)

(58) Field of Classification Search
CPC ............ A61B 17/0218; A61B 17/0206; A61B 17/282–2841
See application file for complete search history.

(56) References Cited

U.S. PATENT DOCUMENTS

| | | | | |
|---|---|---|---|---|
| 3,391,690 | A * | 7/1968 | Armao ............... | A61B 17/2812 83/171 |
| 5,891,017 | A * | 4/1999 | Swindle ............. | A61B 17/0218 600/219 |
| 2004/0024291 | A1* | 2/2004 | Zinkel ................ | A61B 17/0206 600/218 |
| 2007/0219582 | A1* | 9/2007 | Brunelle ............ | A61B 17/8872 606/207 |

(Continued)

OTHER PUBLICATIONS

International Search Report dated Sep. 10, 2018 issued in PCT International Patent Application No. PCT/IT2018/000068, 3 pp.

*Primary Examiner* — Tessa M Matthews
(74) *Attorney, Agent, or Firm* — Nixon & Vanderhye P.C.

(57) ABSTRACT

A multifunctional surgical instrument for extension of laparotomic, laparoscopic, robotic and thoracotomic incisions allows at the same time the spreading apart of the cutaneous/subcutaneous corners, pinching and lifting of the deep parietal layer, its dissection with the electrosurgical knife and protection of the surrounding and underlying tissues, particularly the intestinal ansae in the peritoneal cavity, during the dissection itself.

5 Claims, 5 Drawing Sheets

(56) References Cited

U.S. PATENT DOCUMENTS

Figure 4:
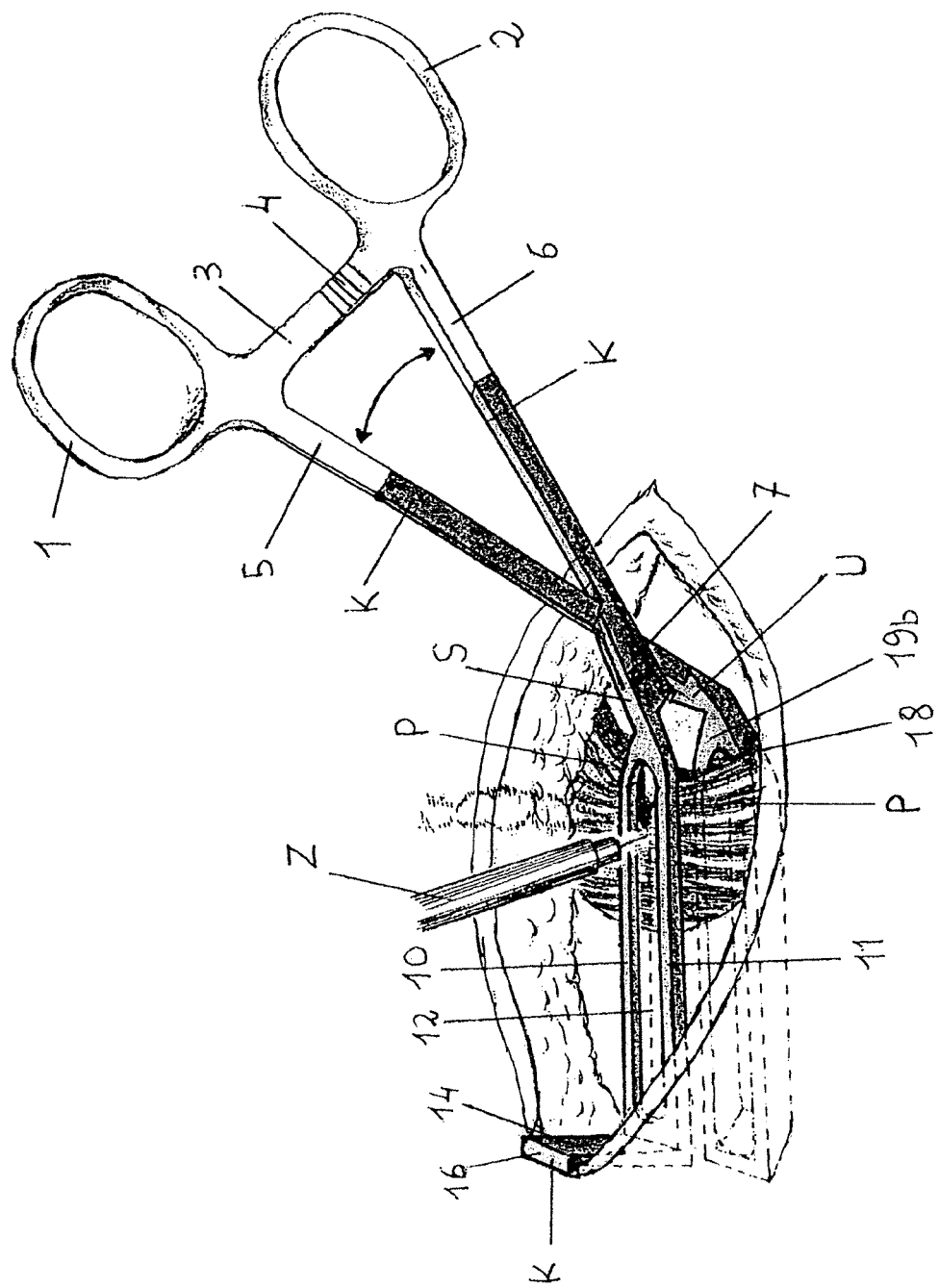

| | | | |
|---|---|---|---|
| 2007/0299315 A1* | 12/2007 | Geller | A61B 17/0206 |
| | | | 600/217 |
| 2011/0282158 A1 | 11/2011 | Anthony et al. | |
| 2012/0059407 A1* | 3/2012 | Isch | A61B 17/282 |
| | | | 606/205 |
| 2015/0100080 A1 | 4/2015 | Kohler | |
| 2015/0119648 A1 | 4/2015 | Barnett et al. | |
| 2017/0007226 A1 | 1/2017 | Fehling | |
| 2019/0007226 A1* | 1/2019 | Johnsen | H04L 49/358 |

* cited by examiner

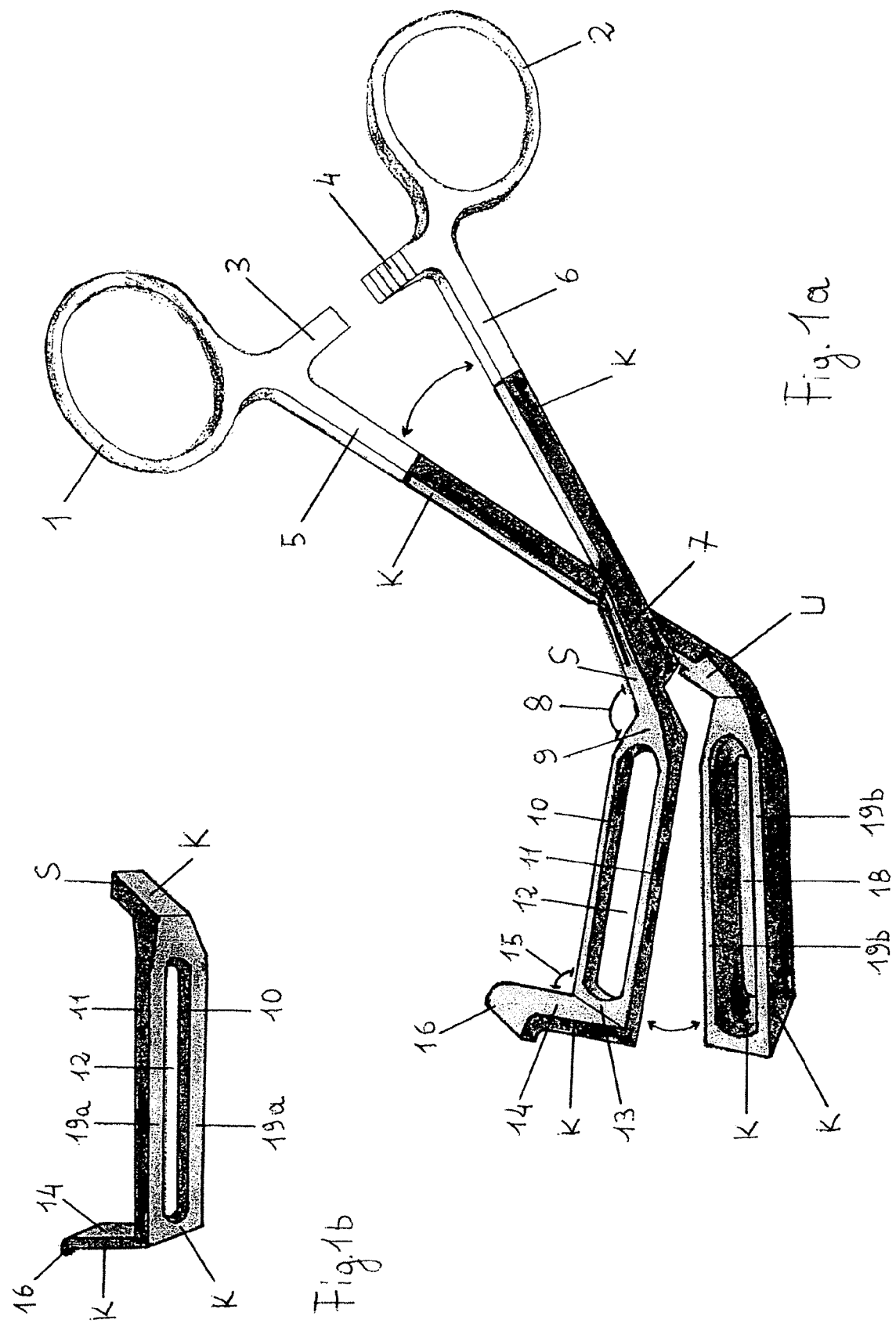

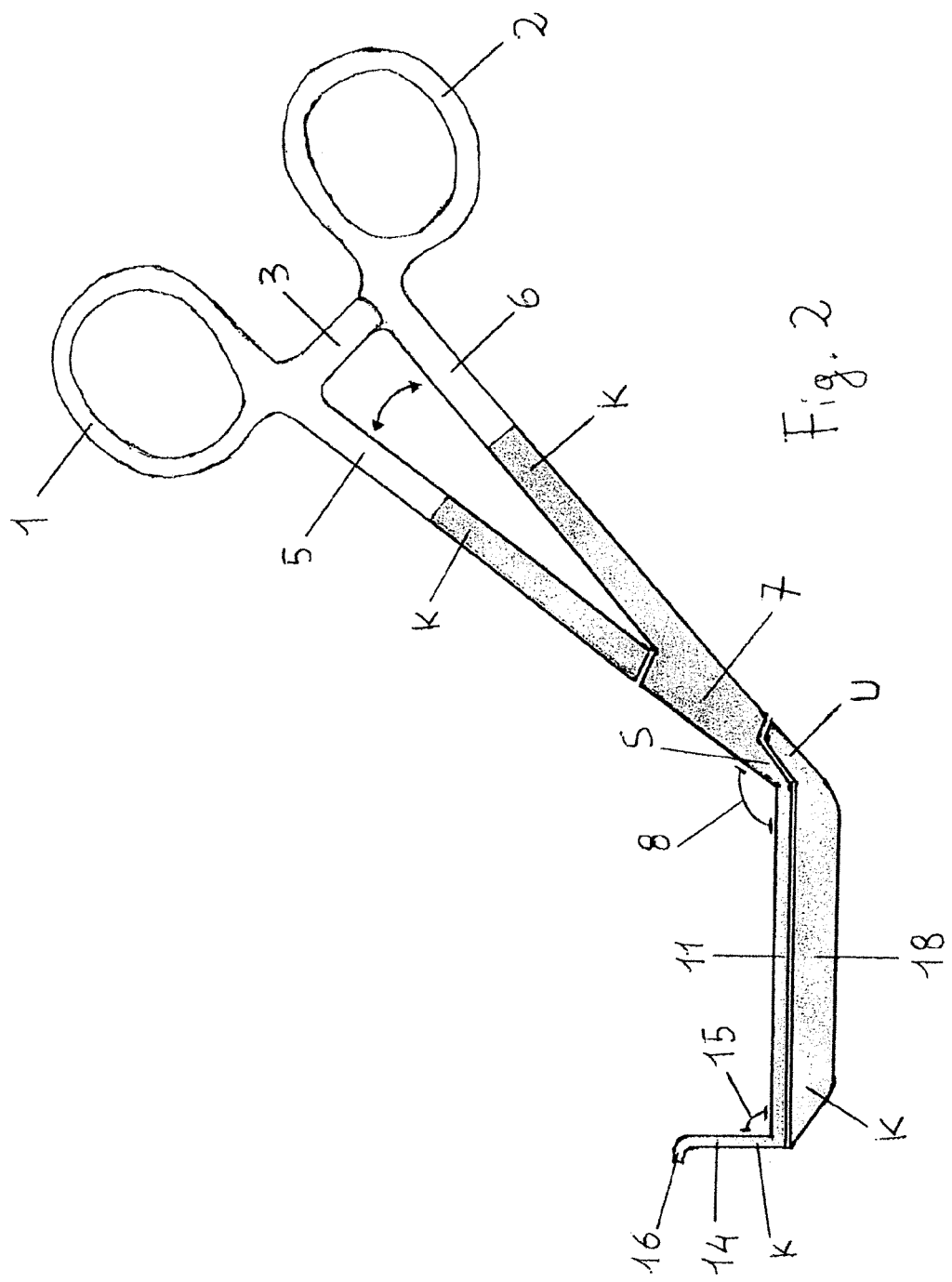

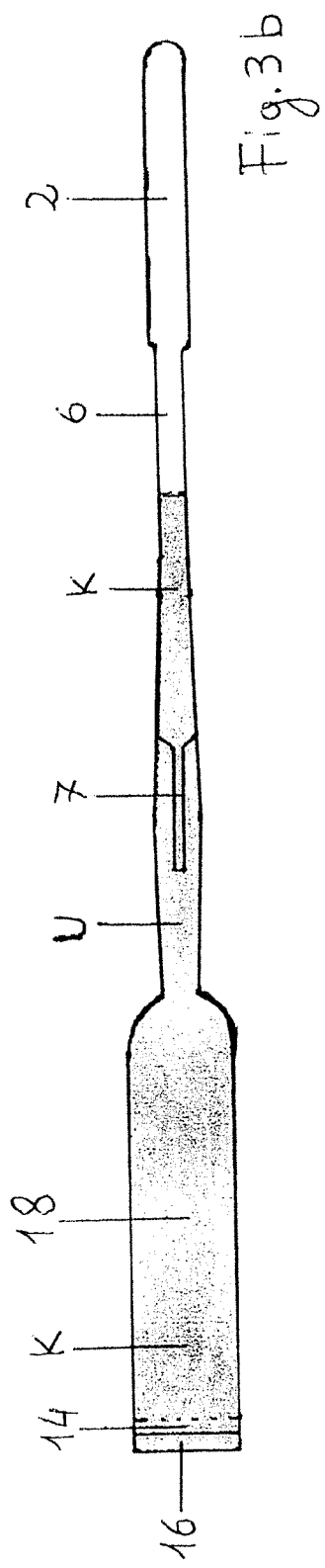
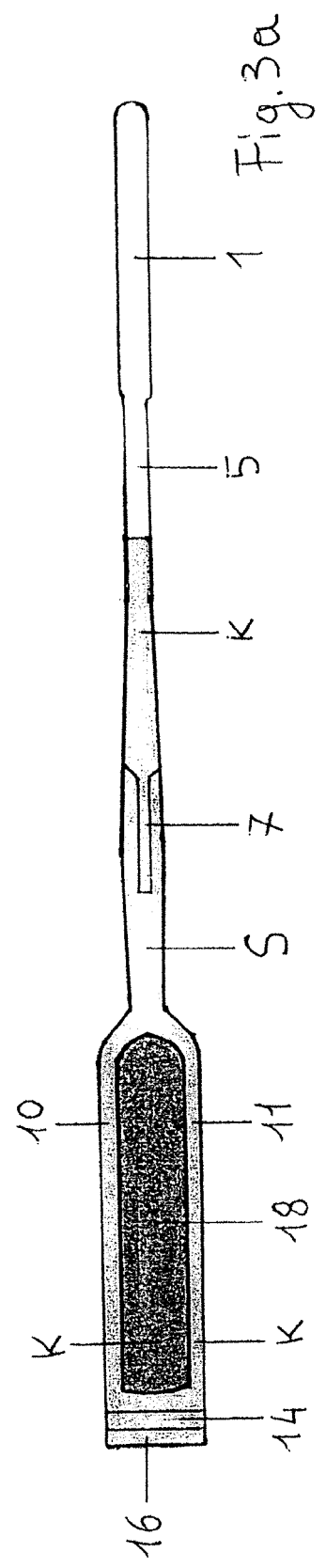

MULTIFUNCTIONAL SURGICAL INSTRUMENT

This application is the U.S. national phase of International Application No. PCT/IT2018/000068 filed May 9, 2018 which designated the U.S. and claims priority to Italian Patent Application No. 102017000057439 filed May 26, 2017, the entire contents of each of which are hereby incorporated by reference.

1) APPLICATION FIELD

Medical Science

2) STATE OF THE ART

The incision of the abdominal wall commonly referred to as laparotomy defines any surgical opening of the abdomen through which the peritoneal cavity can be reached. There are various laparotomic incisions. The correct choice of a lapatotomy incision by the surgeon must follow practical criteria based on two fundamental principles:
A) Wide and sufficient exposure of the operating field;
B) Minimal aesthetic damage.

Point A regards indication and performance of the right choice of surgical incision of the abdominal wall, i.e., the one able to provide the best visibility of the abdominal cavity; this is conditioned by the clinical examination of the patient and the degree of preoperative diagnostic precision.

Point B refers to keeping the cutaneous incision to the minimum necessary in the case of a small laparotomy, an important decision, especially in the young, children and adolescents, and in the female sex, to avoid unaesthetic surgical scars.

The cutaneous incision is the first step in every surgical intervention, after which the manoeuvres can be initiated to access the peritoneal cavity, where the surgical act is performed.

The laparotomic incisions, in relation to their trajectory, are subdivided into vertical, oblique and transversal; they are also called simple, if formed by one segment, or complex, when resulting from multiple simple segments.

At present, one of the surgical interventions more frequently and universally performed is appendectomy for acute appendicitis. This can be performed with laparoscopic or laparotomic technique. Although the choice between the two approaches is individual and pertaining the experience of each surgeon, the laparotomic access remains highly indicated, if not compulsory, in the most acute forms, where it is fundamental, for a positive outcome of the intervention, to have a sufficiently wide operating field for a better visibility and increased freedom of movements. Among the laparotomic accesses, the Mac Burney's incision remains the classic and most frequently employed.

It consists of a small oblique incision in the right iliac fossa, performed perpendicularly to the line connecting the antero-superior right iliac spine with the umbilicus, located at the point of junction of the median third with the external third of the line itself, with a mean length of 3-4 cm (with some variability in length proportional to the adiposity of the patient).

The intervention starts by incising the skin and subcutaneous adiposity till the aponeurosis of the great oblique muscle, which is incised along the course of the fibers for the whole length of the cutaneous incision. While the two borders of the aponeurosis incision are maintained wide apart, a blunt stretching apart is performed of the fibers of the small oblique muscle first and of the transverse muscle subsequently, until the preperitoneal adipose tissue is reached. After incising the trasversalis fascia and the parietal peritoneum, the peritoneal cavity is reached. Once inside the cavity, when the appendix is not immediately detected and/or its search is difficult, in the case of acute phlegmonic or gangrenous appendicitis, with circumscribed peritonitis or in particular situations of abnormal anatomical locations of the coecum and appendix, it is very difficult to dictate specific rules to render the operation typical. The positive outcome of the intervention then depends on the skills of the surgeon, his ability and decisional promptness to derive from his experience, and then apply, all the technical solutions aimed at finding, externalizing and removing the appendix.

In all these cases, the first and most important act is to extend the surgical incision to obtain a wider exposure of the operating field, preferably avoiding a further skin incision.

3) TECHNICAL PROBLEM the most important technical problem in oblique laparoscopic incisions, such as Mac Burney's one, but also other types of small laparotomies, regards the fact that only limited extensions of the surgical wound are possible without further extending the cutaneous incision. Furthermore, these extensions can be performed only through complex procedures, involving the use of multiple monofunctional instruments/devices, this increases the duration of the intervention and involves the risk of reduced precision during the section of the deep parietal layer (fascia, muscles, parietal peritoneum), reduced protection of the tissues and intestinal ansae of the peritoneal cavity, and when the incision is extended also to the skin, anaesthetic scar outcomes, particularly problematic in children, adolescents and women. At present, to be able to extend a small laparotomic incision without further incising the skin, it is necessary firstly to insert some gauze pads (device 1) into the peritoneal cavity to protect the ansae from the energy delivered by the electricrosurgical knife, then to stretch apart the cutaneous and subcutaneous borders at the angles of the surgical wound using one or more retractors (instrument 2), subsequently to insert a thumb forceps with open branches (instrument 3) into the peritoneal cavity, over the gauze pads, to strain and lift the deep parietal layer and then to proceed with the section of the parietal layer itself with the tip of the electrosurgical knife along the main direction of the incision without the help of a guide. With this technique of extension of the incision confined to the deep parietal layer (fascia, muscles, parietal peritoneum), a better exposure of the peritoneal cavity is obtained through multiple steps with different instruments and furthermore at the expense of the precision of the section of the deep layer and of the protection of the tissues, with the potential risk of lesions of the intestinal ansae, and also at the expense of the optimal duration of the intervention.

4) SOLUTIONS TO THE TECHNICAL PROBLEM

The invented surgical instrument is multifunctional, it allows the concurrent performing of a number of functions which would normally require the use of multiple instruments/devices: it protects the intestinal ansae insulating them from the deep parietal layer to be incised (replacing the function of the gauze pads, device 1), stretches apart the cutaneous/subcutaneous borders (replacing the retractor, instrument 2), pinches and lifts the deep parietal layer (replacing the thumb forceps, instrument 3) and provides a guide binary along which the section can be performed (further function, 4). This surgical instrument facilitates the procedure of extension of any small laparotomy, particularly that of Mac Burney, and renders it more precise and safer. The first surgeon himself manoeuvers the instrument, at the same time he: (1) spreads apart the cutaneous/subcutaneous borders at the corners of the surgical wound and, by modulating the strength impressed to the instrument itself, he can regulate the optimal extension that allows the lengthening of the necessary centimeters of the small laparotomy so to obtain the most favourable exposure of the operating field; the skin is therefore not further incised and unaesthetic scars are avoided; (2) pinches, tightens and lifts the deep parietal layer; (3) incises the deep parietal layer with the electrosurgical knife precisely along the guide binary, created by the opening of the two small arms of the upper prong, avoiding the risk of lesioning of the underlying and surrounding structures. In synthesis, a sufficient exposure of the peritoneal cavity is obtained with precision, safety, without aesthetic damage and with a reduction of the operating time.

5) FIGURES

FIG. 1a: surgical instrument with open bite, lateral vision; blunt upper surface of the borders of the lower prong, atraumatic FIG. 1b: detail of the upper prong of the bite, with blunt surface of the inferior borders of the bite, atraumatic FIG. 2: surgical instrument with closed bite; lateral vision FIG. 3a: surgical instrument with closed bite; vision from above FIG. 3b: surgical instrument with closed bite; vision from below FIG. 4: surgical instrument in use FIG. 5a: detail of the handle of the surgical instrument, with stop self-retaining rack indicated with the letter R FIG. 5b: detail of the handle of the surgical instrument, without stopper or free

6) DESCRIPTION OF THE FIGURES

FIG. 1a shows the invented surgical instrument, shaped as a hemostatic clamp of short-medium length, constituted by a ring handle 1,2, with toothed rack stopper 3,4, two straight articulated branches, one upper branch 5, and one lower branch 6. The upper branch 5, and the lower branch 6, after the hub 7, both extend to constitute the prongs of the surgical bite, indicated with the letters S, U, and then become bent at the same level with an angle of 130 degrees 8. The lower branch 6 extends to form the upper prong of the bite S, in the shape of a ribbon-like flat lamina 9 similar to that of a ribbon-like retractor, which immediately divides into two small arms 10,11, of identical shape and length, which course parallel, creating between them a central fenestration 12, and at their reunification, reconstitute a ribbon-like lamina 13, similar to the initial one 9, with blunt surface of the inferior borders 19a of the two small arms 10,11 providing atraumatic grip FIG. 1b, which terminates immediately after in an L ribbon-shaped, upwards facing, retractor 14, with a paddle angled at 90 degrees 15, terminating at the top with a slight outwards angulation 16. The upper branch 5, extends, after the hub 7, to form the lower prong U of the bite, at the same level as the upper lamina 9, always with the same angulation 8, in the shape of a curved concave valve 18, with the same width and length of the upper prong S with blunt upper surface of the borders 19b, providing atraumatic grip, and, at closed bite, with the surfaces of the two prongs fitting together perfectly FIG. 2, 3a, 3b. All the components of the surgical instrument situated distally to the upper third of the branches of the handle are covered with high technology insulated coating, shown in the FIGS. 1a, 1b, 2, 3a, 3b, 4, 5a and 5b with shaded grey color, indicated with the letter K.

7) FUNCTIONING instrument with open bite, the lower prong U of the bite is inserted into the peritoneal cavity with the upper surface 19b tangent the parietal peritoneum, while the lower surface 19a of the upper prong S rests on the deep parietal layer P, formed by fascia, muscles and parietal peritoneum, both prongs embrace the layer without tightening it, while the curved paddle angled at 90 degrees of the upper prong, shaped as an L ribbon-like retractor, upwards oriented 14, with which it terminates, is pushed against the cutaneous/subcutaneous borders of one angle to open wide and keep them opened, allowing the uncovering of the deep parietal layer which has to be incised.

Once the optimal extension is reached, the bite is tightened, and the deep parietal layer P is pinched and lifted. At this point the deep parietal layer P can be incised, with the electrosurgical knife Z, through the central fenestration 12 of the upper prong S of the bite which serves as a guide FIG. 4.

The surfaces of the upper borders 19b, with atraumatic blunt grip, of the curved concave valve 18 of the lower prong U of the bite adhere perfectly to the parietal peritoneum, and the concavity of the valve 18 allows a possible downward excursion of the tip of the electrosurgical knife Z and, during the section, protects all the underlying and adjacent structures FIG. 4, particularly the intestinal ansae. If a further extension of the incision is necessary, the whole described procedure can be repeated at the opposite angle.

8) INDUSTRIAL APPLICATION the invented instrument can be employed in all types of laparotomic surgical interventions, laparoscopic interventions and eventually also thoracoscopic interventions in operating rooms of divisions of: general surgery, paediatric surgery (in miniaturized form, baby, short), emergency surgery, digestive surgery, urologic surgery, vascular surgery, thoracic surgery, plastic surgery, laparoscopic surgery, robotic surgery, and in every other use in any other surgical branch (particularly in laparotomic interventions of appendectomy, with incision according to Mac Burney).

9) ADVANTAGES the multifunctionality of the surgical instrument offers several concurrent advantages: (A) safe protection of the intestinal ansae and all the surrounding tissues during the section with the electrosurgical knife; B) spreading apart of skin/subcutis; (C) atraumatic grip of the deep parietal layer to be incised; D) guide to direction of the incision procedure of the deep parietal layer with the electrosurgical knife. The instrument thus offers the advantages of facilitating, rendering more precise, safer and more rapid (reduction of the operating time) the surgical manoeuver of extension of a small laparotomy, without further incision of the skin.

A) The invented surgical instrument is advantageous because it protects the intestinal ansae in the peritoneal cavity during the section of the deep parietal layer (fascia—muscles—parietal peritoneum) with the electrosurgical knife, thanks to the curved concave valve of the lower prong of the bite. When the bite tightens the deep parietal layer, the upper borders of the valve adhere perfectly to the parietal peritoneum, the concavity of the valve allows a possible downward excursion of the tip of the electrosurgical knife during the incision, protecting all the underlying and adjacent structures.

Being provided with a high technology insulating coating, the instrument furthermore prevents any possible transmission of the electrical energy to the surrounding structures during the section of the deep parietal layer by the electrosurgical knife, allowing the first operator surgeon to incise this layer in safe conditions.

B) The invented surgical instrument is advantageous because it facilitates the manoeuver of the spreading apart of the cutaneous/subcutaneous borders, eventually at both corners of a small laparotomy, allowing the exposure of the deep parietal layer to be incised (fascia, muscles, parietal peritoneum). The first surgeon, by personally maneuvering the instrument, can modulate the strength to be impressed to the instrument itself to spread apart the cutaneous borders, being able to regulate the right extension which permits the gain of the necessary centimeters of opening of the small laparotomy, thus obtaining the most favourable exposure of the operating field, with savings of the cutaneous incision and avoidance of unaesthetic scars.

C) The invented surgical instrument is advantageous because, thanks to the blunt surface of the borders of the two prongs of the bite, it allows an atraumatic grip of the deep parietal layer to be incised.

D) The invented surgical instrument is advantageous because it provides a precise orientation guide for the section of the fascia—muscles—parietal peritoneum, allowing the tip of the electrosurgical knife to easily cut the deep parietal layer through the central opening of the upper prong, formed by small arms which act as a binary guide.

Figure 5B:
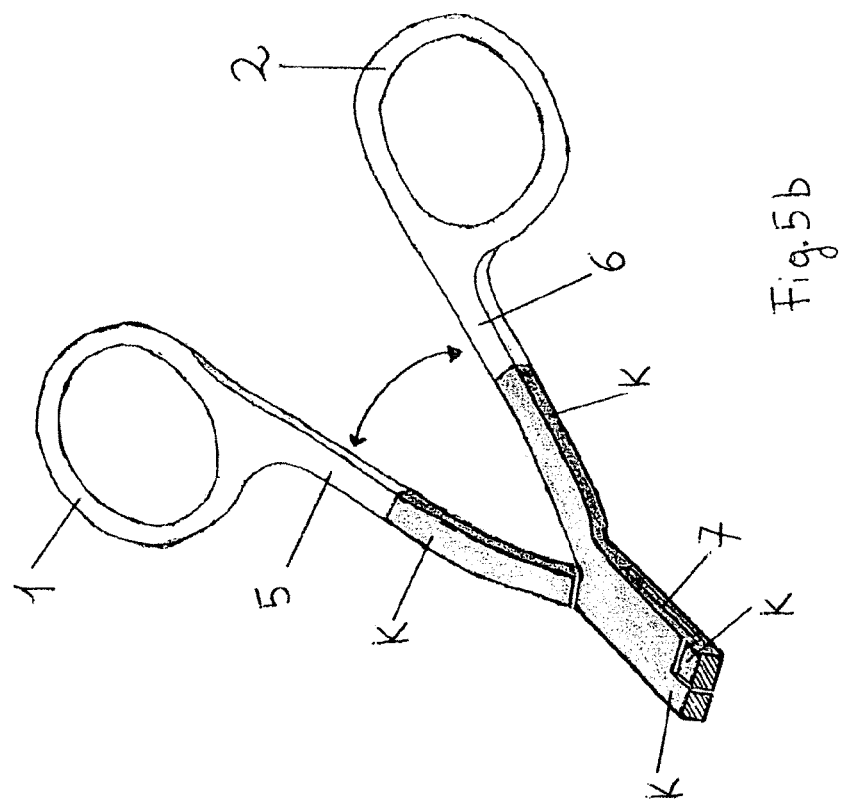
Figure 5A:
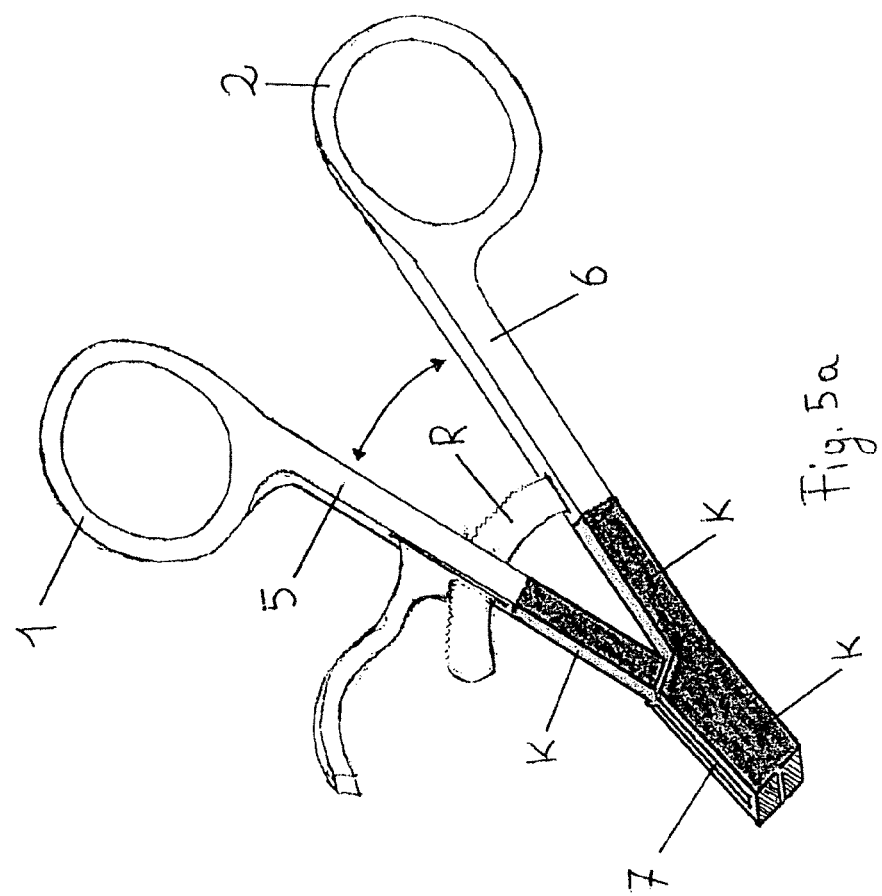

10) VARIANTS variants can be performed in the handle stopper: with toothed rack stopper FIG. 5a, without stop or free FIG. 5b. Furthermore a short or baby instrument can be conceived for the use in paediatric surgery.

The invention claimed is:

1. Multifunctional surgical instrument for extension of laparotomic, laparoscopic, robotic and thoracotomic incisions, comprising a handle including, one upper ring and one lower ring, and two straight articulated branches consisting of one upper branch and one lower branch, wherein the two straight articulated branches are connected to each other through a hub both extend to constitute two prongs of a bite consisting of one upper prong and one lower prong, wherein the lower straight branch extends to constitute the upper prong of the bite which, after an angle of approximately 130 degrees, becomes shaped as an L ribbon-like retractor, centrally fenestrated with a paddle angulated at 90 degrees, facing upwards, terminating at the top with an outwards angulation, which is thereby configured to spread apart cutaneous/subcutaneous corners of a surgical wound, and to incise a deep parietal layer, wherein the upper straight branch extends to constitute the lower prong of the bite which, too, after an angle of approximately 130 degrees at the same level as the angle of the upper prong, becomes shaped as a curved concave valve, that is configured to ensure protection of surrounding tissues and underlying organs in a peritoneal cavity, particularly intestinal ansae during a section with an electrosurgical knife, with all components of the surgical instrument situated distally to an upper third of the straight articulated branches of the handle being covered with electrically insulating coating.

2. Surgical instrument according to claim 1, wherein the upper prong of the bite, shaped as a ribbon-like flat lamina, immediately after its formation, divides into two arms of identical shape and length, which course parallel, creating among them the central fenestration serving as a guide for the electrosurgical knife.

3. Surgical instrument according to claim 1, wherein grip surfaces of the two prongs of the bite are blunt, allowing an atraumatic grip of the deep parietal layer when the bite is tightened.

4. Surgical instrument according to claim 1, wherein all its components distal to the upper third of the handle are covered with electrically insulating coating, configured to avoid transmission and propagation of electricity produced by the electrosurgical knife during its use.

5. Surgical instrument according to claim 1, further comprising a toothed rack stopper.

* * * * *